US011351314B2

(12) United States Patent
Kessler et al.

(10) Patent No.: US 11,351,314 B2
(45) Date of Patent: Jun. 7, 2022

(54) INHALER AND FLUID RESERVOIR FOR AN INHALER

(71) Applicant: HAUNI MASCHINENBAU GMBH, Hamburg (DE)

(72) Inventors: Marc Kessler, Hamburg (DE); Rene Schmidt, Buchholz i.d.N. (DE)

(73) Assignee: HAUNI MASCHINENBAU GMBH, Hamburg (DE)

( * ) Notice: Subject to any disclaimer, the term of this patent is extended or adjusted under 35 U.S.C. 154(b) by 631 days.

(21) Appl. No.: 16/324,430

(22) PCT Filed: Aug. 3, 2017

(86) PCT No.: PCT/EP2017/069667
§ 371 (c)(1),
(2) Date: Feb. 8, 2019

(87) PCT Pub. No.: WO2018/029077
PCT Pub. Date: Feb. 15, 2018

(65) Prior Publication Data
US 2019/0167923 A1 Jun. 6, 2019

(30) Foreign Application Priority Data
Aug. 9, 2016 (DE) .................... 10 2016 114 718.4

(51) Int. Cl.
*A61M 11/04* (2006.01)
*A61M 11/00* (2006.01)
(Continued)

(52) U.S. Cl.
CPC ......... *A61M 11/042* (2014.02); *A24F 40/485* (2020.01); *A24F 40/57* (2020.01);
(Continued)

(58) Field of Classification Search
CPC .................. A61M 11/042; A61M 15/0055
(Continued)

(56) References Cited

U.S. PATENT DOCUMENTS 5,894,484 A    4/1999  Voges
5,894,841 A *  4/1999  Voges ................ B01F 15/0255
                                                128/203.12
(Continued)

FOREIGN PATENT DOCUMENTS

CN        1127983 A      11/2003
CN      105142444 A      12/2015
(Continued)

OTHER PUBLICATIONS

German Examination Report issued by the German Patent Office dated May 5, 2017 for corresponding German Application No. 102016114718.4, filed Aug. 9, 2016, which the subject application claims priority from (7 pages).
(Continued)

*Primary Examiner* — Alexander Gilman
(74) *Attorney, Agent, or Firm* — Saliwanchik, Lloyd & Eisenschenk

(57) ABSTRACT

The invention relates to an inhaler comprising a housing with a mouth end, at least one air inlet opening and an air channel extending into the housing between the at least one air inlet opening and the mouth end, a receiving area for a fluid reservoir, an electric energy accumulator, a supply device for generating steam and/or aerosol from a component mixture extracted from the fluid reservoir and adding the steam and/or the aerosol to an air flow flowing into the air channel, wherein the supply device comprises an evaporator which can be controlled separately and a control device for controlling the supply device. The control device is connected or can be connected a data store in which at least
(Continued)

one set predefining the evaporating parameters can be called upon and stored therein for evaporating the component mixture in the evaporator.

20 Claims, 4 Drawing Sheets

(51) Int. Cl.
    *A61M 15/00*         (2006.01)
    *A61M 15/06*         (2006.01)
    *A24F 40/485*       (2020.01)
    *A24F 40/57*         (2020.01)
    *A61M 16/00*         (2006.01)
    *A24F 40/10*         (2020.01)

(52) U.S. Cl.
    CPC ...... *A61M 11/005* (2013.01); *A61M 15/0065* (2013.01); *A61M 15/06* (2013.01); *A24F 40/10* (2020.01); *A61M 11/001* (2014.02); *A61M 2016/0024* (2013.01); *A61M 2205/3368* (2013.01); *A61M 2205/3389* (2013.01); *A61M 2205/3653* (2013.01); *A61M 2205/50* (2013.01); *A61M 2205/6018* (2013.01); *A61M 2205/8206* (2013.01)

(58) Field of Classification Search
    USPC ........................................................ 131/328
    See application file for complete search history.

(56) References Cited

U.S. PATENT DOCUMENTS

| | | | |
|---|---|---|---|
| 2005/0016550 A1 | 1/2005 | Katase | |
| 2006/0196518 A1 | 9/2006 | Hon | |
| 2013/0284192 A1 | 10/2013 | Peleg et al. | |
| 2014/0014126 A1 | 1/2014 | Peleg et al. | |
| 2014/0096782 A1* | 4/2014 | Ampolini | A24F 40/60 |
| | | | 131/328 |
| 2014/0190496 A1* | 7/2014 | Wensley | A24B 15/167 |
| | | | 131/273 |
| 2014/0321837 A1* | 10/2014 | Flick | A61M 15/06 |
| | | | 392/387 |
| 2014/0345635 A1 | 11/2014 | Rabinowitz et al. | |
| 2016/0021930 A1 | 1/2016 | Minskoff et al. | |
| 2016/0021931 A1 | 1/2016 | Hawes et al. | |
| 2016/0022930 A1* | 1/2016 | Greim | A61M 15/0035 |
| | | | 131/328 |
| 2016/0057811 A1* | 2/2016 | Alarcon | A24F 40/50 |
| | | | 219/494 |
| 2016/0205998 A1* | 7/2016 | Matsumoto | A24F 40/20 |

FOREIGN PATENT DOCUMENTS

| | | |
|---|---|---|
| DE | 202013010986 | 2/2014 |
| DE | 20 2014 101 125 U1 | 6/2014 |
| EP | 2 399 636 A1 | 12/2011 |
| JP | H08-511966 A | 12/1996 |
| JP | 2015-524260 A | 8/2015 |
| JP | 2015-531235 A | 11/2015 |
| JP | 2016-501588 A | 1/2016 |
| JP | 2016-520061 A | 7/2016 |
| WO | WO 95/01137 A1 | 1/1995 |
| WO | WO 2014/085719 A1 | 6/2014 |
| WO | WO 2014/102091 A1 | 7/2014 |
| WO | WO 2014/182736 A1 | 11/2014 |

OTHER PUBLICATIONS

First examination report issued by the European Patent Office dated Apr. 23, 2020 for parallel European Patent Application No. 17 751 068.2.
First examination report issued by the Japanese Patent Office dated Mar. 17, 2020 for parallel Japanese Patent Application No. 2019-507279.
Examination Report issued by the European Patent Office dated Jun. 16, 2021 for parallel European Patent Application No. 17 751 068.2.
Examination Report issued by the Chinese Patent Office dated Mar. 10, 2021 for parallel Chinese Patent Application No. 201780049012.5.

\* cited by examiner

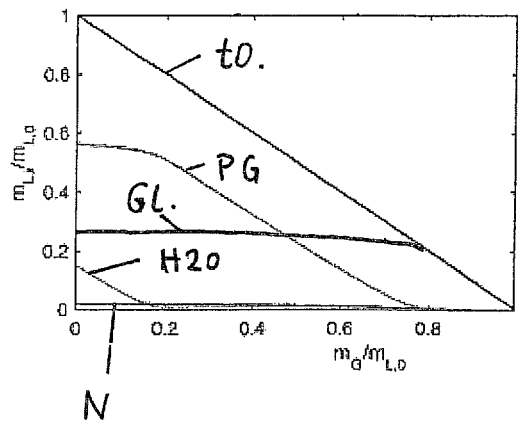
Fig. 4A
Fig. 4B
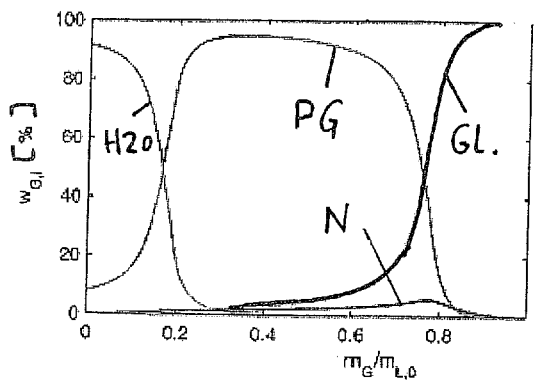
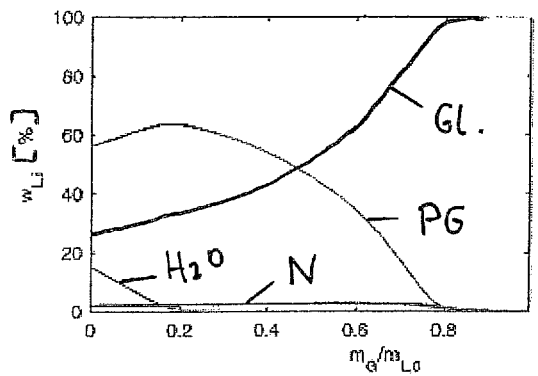
Fig. 4C
Fig. 4D
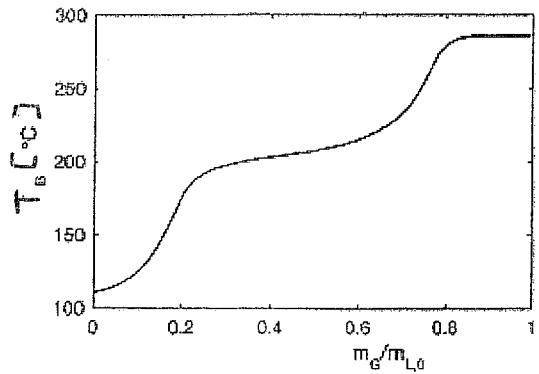

INHALER AND FLUID RESERVOIR FOR AN INHALER

CROSS REFERENCE TO RELATED APPLICATIONS

This application is a National Stage Application of International Application Number PCT/EP2017/069667, filed Aug. 3, 2017; which claims priority to German Patent Application No. 102016114718.4, filed Aug. 9, 2016.

The present invention relates to an inhaler comprising a housing with a mouth end, at least one air inlet opening and an air channel extending in the housing between the at least one air inlet opening and the mouth end, a receiving area for a fluid reservoir, an electrical energy source, a supply device for generating vapor and/or aerosol from a component mixture extracted from the fluid reservoir and adding the vapor and/or the aerosol to an air flow flowing in the air channel, wherein the supply device has an evaporator which can be actuated separately and a control device for controlling the supply device.

Most of the electronic cigarette products currently available on the market are based on the so-called wick filament principle. A heating filament is partially wrapped around a wick made of glass fiber for example, said wick being in contact with a fluid reservoir. When the heating filament is heated, the fluid located in the wick, which is also referred to as liquid, evaporates in the region of the heating filament. Due to capillary action, the evaporated fluid is subsequently delivered from the fluid reservoir. Such an electronic cigarette is described, by way of example, in US 2016/0021930 A1.

A range of problems occur with these systems. Firstly, the subsequent capillary delivery of the liquid is coupled to the quantity of liquid evaporated and the physical properties of the individual components of the component mixture. There is a risk of overheating ("hot puff") if the heating capacity exceeds the delivery rate, because the maximum delivery rate and evaporative capacity are consequently physically limited.

Secondly, due to physical constraints, the temperature in these systems cannot obviously be adjusted over the length of the heating filament, or respectively at the location and over the time of the evaporation, so that homogeneous evaporation cannot be achieved in the entire system.

Thirdly, the temperature cannot be restricted locally, resulting in a risk of overheating due to inhomogeneous liquid utilization before and during a puff and, in connection therewith, pollutants are emitted and liquid is explosively released.

Fourthly, a segregation which is dependent on the configuration of the system and on the liquid composition takes place and, consequently, the concentration of the component mixture changes, resulting in an unwanted changeable active ingredient release per puff.

The object of the invention is to provide an inhaler and a fluid reservoir therefor, in which one or more of the previously described disadvantages are avoided.

The invention achieves this object with the features of the independent claims.

According to the invention, the control device is, accordingly, connected to a data store, in which at least one set of predefined evaporating parameters is stored and can be called upon for evaporating the component mixture in the evaporator.

The invention has identified, based on theoretical considerations, and practically proven, by way of example by measurements, that an obvious and universal relationship exists between the liquid composition, the temperature behavior during evaporation, which is due in particular to the evaporator technology used, and the active ingredient release.

One aspect of the invention consists of converting this realization into a method of controlling the evaporation of the component mixture by means of the set of evaporating parameters stored in the data store. The known evaporation temperature and known system status are directly connected to one another by means of the properties of the component mixture. The heating capacity obtained at any point of the evaporation consequently allows a direct conclusion to be drawn regarding the current liquid or respectively vapor composition. This knowledge can, in turn, be used to control the evaporation of the component mixture.

A further aspect of the invention consists of a targeted fluid composition in order to influence the active ingredient release at a given or respectively adjusted threshold temperature (maximum temperature) of the evaporator. This means that the change in concentration of the component mixture can be controlled completely and/or a segregation of the fluid components can be prevented. In addition, it is possible to avoid overheating and the associated emission of pollutants.

Further aspects of the invention relate to the delivery of the liquid and/or the evaporation. The liquid is advantageously actively delivered, for example by means of micromechanical pumps, or passively, for example by microfluidic capillary action. The evaporation advantageously takes place by means of a heating device decoupled from the supply, for example a heating surface, in particular on the basis of MEMS (Micro-Electro-Mechanical System), which is controlled or regulated at the (maximum) evaporation temperature required in each case.

The at least one set of predefined evaporating parameters can, in particular, be deduced from the liquid phase-gas phase equilibrium diagram of the component mixture or correspond thereto.

The at least one set of predefined evaporating parameters preferably contains data regarding one or more variables from the following group of variables: a temperature to be adjusted, in particular the temperature of the evaporator or respectively of the heating device; a duration of individual evaporation steps and/or the entire evaporation process in the evaporator, which is to be adjusted; a pressure to be adjusted, in particular in the atomizer; an evaporation energy to be provided for the evaporator. The at least one set of predefined evaporating parameters more preferably contains data regarding one or more variables from the following group of variables: a minimum temperature and/or a maximum temperature; a minimum pressure and/or a maximum pressure; a minimum duration and/or a maximum duration of individual evaporation steps and/or of the entire evaporation process. In order to adjust a predefined temperature, the evaporator preferably comprises a heating device. The evaporator can advantageously have a temperature sensor for measuring the temperature of the heating device and/or for controlling or respectively regulating the temperature of the heating device.

In one preferred embodiment of the invention, the predefined temperature is variable within an evaporation interval, in particular it intermittently increases and/or intermittently falls and/or is intermittently constant over the duration of an evaporation interval. As a result, an unwanted changeable active ingredient release, in particular by means of a puff, can be counteracted.

In a further preferred embodiment of the invention, the temperature of the evaporator or respectively of the heating device is kept, at least over an evaporation interval corresponding to an inhalation puff, above a first characteristic temperature, in particular the boiling temperature of a component of the component mixture. The predefined temperature value advantageously lies, in this case, in the range between 1% and 90%, preferably 3% to 70%, particularly preferably 5% to 50% above the first characteristic temperature. If necessary, this aspect can only be protected independently, i.e. in a form which refers back to the preamble of Claim 1.

A maximum temperature of the evaporator is preferably at most 350° C., more preferably at most 300° C. and, particularly preferably, at most 290° C. Thanks to this measure, the development of pollutants due to overheating can be counteracted.

In a likewise preferred embodiment of the invention, the temperature of the evaporator or respectively of the heating device is kept, at least over an evaporation interval, below a second characteristic temperature, in particular the boiling temperature of a component of the component mixture. In this case, the second characteristic temperature is preferably the boiling temperature of a component which boils higher than an active ingredient component, advantageously of the highest-boiling component of the component mixture. If necessary, this aspect can only be protected independently, i.e. in a form which refers back to the preamble of Claim 1. In this embodiment, the proportion of a component which boils higher than an active ingredient component can be deliberately used in the manner of an adjusting screw, in order to dose the strength of the active ingredient supply per puff and, for example, to increase it with respect to a strength which results purely mathematically from the mass fraction of the active ingredient in the component mixture. This effect is produced in that the (dummy) component which boils higher than the active ingredient cannot appreciably evaporate, such that the evaporative capacity is concentrated on the lower boiling components including the active ingredient.

In this case, the evaporation interval preferably has a duration of 1 to 12 seconds, more preferably 2 to 8 seconds.

In a further embodiment of the invention, a machine-readable identification of the component mixture is assigned to the fluid reservoir. The control device can read out the identification, read out the relevant set of evaporating parameters from the data store and use these as the basis for controlling the evaporation of the component mixture. The identification can include details regarding the type of liquid, nicotine proportion, smoker profile, batch number, production date and/or best before date.

In particular, during an application in an electronic cigarette product, the component mixture advantageously contains nicotine as the active ingredient, preferably with a proportion by weight or mass fraction of 0.1% to 2%, preferably from 1% to 2%, particularly preferably 2%, based on the weight of the component mixture. In the case of the active ingredient nicotine, the previously mentioned higher boiling component is, for example, glycerin.

The component mixture preferably contains glycerin and/or 1,2-propylene glycol as the aerosol generator.

The proportion by weight of glycerin and/or 1,2-propylene glycol preferably lies in the region of 50% to 98%. The proportion by weight of glycerin lies, in some embodiments, in the range between 18% and 98%, preferably between 26% and 87%, particularly preferably between 26% and 50%, and/or is preferably at least 44 percent by weight, more preferably at least 50 percent by weight, even more preferably at least 55 percent by weight, particularly preferably at least 60 percent by weight, in each case based on the weight of the component mixture. The proportion by weight of 1,2-propylene glycol preferably lies in the range between 0% and 98%, preferably between 20% and 80%, particularly preferably between 40% and 70%, based on the weight of the component mixture.

The component mixture can advantageously contain water, preferably with a proportion by weight of 0% to 30%, preferably of 2% to 20%, particularly preferably of 4% to 13%, based on the component mixture.

For a, if necessary, gradual evaporation of the components, the data store preferably includes, in each case, temperatures to be adjusted, pressures to be adjusted and/or time intervals to be adjusted of individual, if necessary successive, evaporation steps. The at least one set of predefined evaporating parameters advantageously has data regarding a temperature profile which rises or falls incrementally in a graduated manner in sections over time, a time interval profile which rises or falls incrementally in a graduated manner in sections and/or regarding a pressure profile which rises or falls incrementally in a graduated manner in sections.

The evaporation interval is preferably divided into at least two phases, wherein a different quantity and/or different evaporation energy is supplied to the evaporator in a first phase than in a second phase. In this case, the first phase preferably extends over $1/50$ to $2/3$, preferably $1/10$ to $1/2$ of the duration of the evaporation interval. The temperature for the evaporator is preferably variably predefined within one or both phases, in particular it intermittently increases and/or intermittently falls and/or is intermittently constant over the duration of one or within each of the two phases.

In particular, the inhaler according to the invention can be used in one application in a completely handheld form as an electronic cigarette product, or E-cigarette for short, in particular it can be used in the manner of a cigarette in a form where it can be held in one hand, and it is portable and self-contained, in particular network-independent.

The invention will be explained below on the basis of preferred embodiments, with reference to the appended figures, wherein:

FIGS. 4A-4D show diagrams regarding the evaporation behavior of a reference component mixture;

Figure 1:
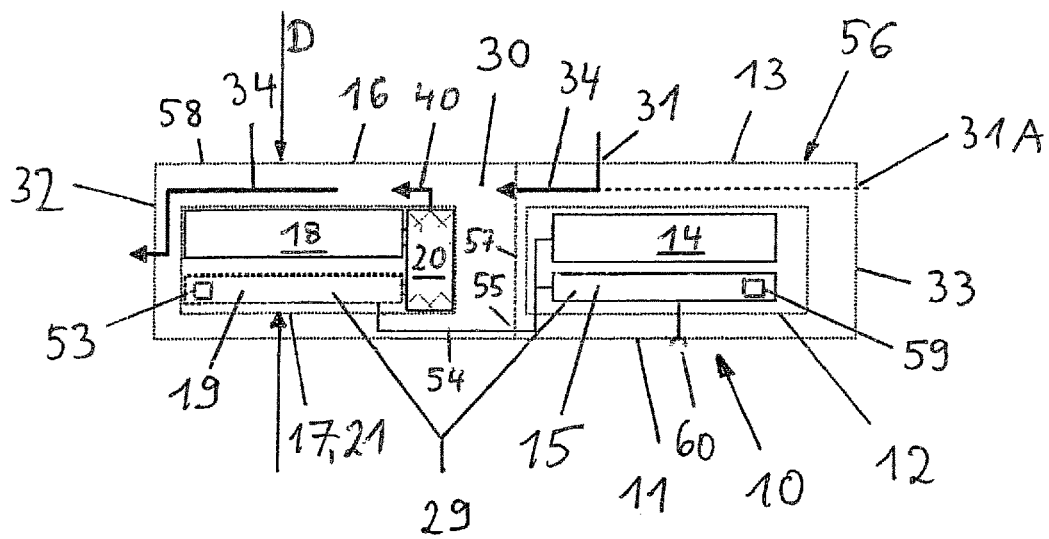
FIG. 1 shows a cross-sectional view of an electronic cigarette product in one embodiment of the invention.

The electronic cigarette product 10 comprises a substantially rod-shaped or cylindrical housing 11. An air channel 30 is provided in the housing 11 between at least one air inlet opening 31 and the mouth end 32 of the cigarette product 10. In this case, the mouth end 32 of the cigarette product 10 designates the end, on which the consumer draws for the purposes of inhaling, thereby applying a negative pressure to the cigarette product and generating an air flow 34 in the air channel 30. At least one air inlet opening 31 can be arranged on the casing side of the housing 11. Additionally or alternatively, at least one air inlet opening 31A can be arranged at the remote end 33 of the cigarette product 10. The remote end 33 of the cigarette product 10 designates the end of the cigarette product 10 opposite the mouth end 32. The air sucked in through the inlet opening 31 is conducted in the air channel 30, if necessary, via the interface or respectively separation plane 57 to the supply device 20. The supply device 20 supplies fluid 50 from the fluid tank 18 as an addition 40 in the form of small drops of fluid as a mist/aerosol and/or in a gaseous form as vapor to the air flow 34.

The cigarette product 10 is preferably designed such that the drawing resistance at the mouth end 32 preferably lies in the range between 50 mm and 130 mm of water, more preferably between 80 mm and 120 mm of water, even more preferably between 90 mm and 110 mm of water and, optimally, between 95 mm and 105 mm of water.

The drawing resistance relates, in this case, to the pressure which is required to draw air through the full length of the cigarette product 10 at a rate of 17.5 ml/s at 22° C. and 101 kPa (760 Torr), and which is measured in accordance with ISO 6565:2011. The cigarette product 10 comprises a first (axial) section 13, advantageously at the remote end 33 of the cigarette product 10, in which an electronic energy supply unit 12 having an electrical energy source 14 and an electrical/electronic unit 15 is arranged. The energy source 14 advantageously extends in the axial direction of the cigarette product 10. The electrical/electronic unit 15 is advantageously arranged laterally next to the energy source 14. The energy source 14 can, in particular, be an electrochemical disposable battery or a rechargeable electrochemical storage battery, e.g. a lithium ion battery.

The cigarette product 10 furthermore comprises a second (axial) section 16, advantageously at the mouth end 32 of the cigarette product 10, in which a consumer unit 17 having a fluid tank 18, an electrical unit 19 and a supply device 20 is arranged or respectively can be arranged. The fluid tank 18 advantageously extends in the axial direction of the cigarette product 10.

A standard electrical/electronic unit, which can be arranged either in the energy supply unit 12 or in the consumer unit 17, can also be provided instead of the separate electrical/electronic units 15, 19. The entirety of the electrical/electronic units of the cigarette product 10 is referred to below as the control arrangement 29.

A sensor, for example a pressure sensor or a pressure or flow switch, is advantageously arranged in the housing 11, wherein the control arrangement can establish an operating status of the cigarette product on the basis of a sensor signal output by the sensor, in that a consumer draws on the mouth end 32 of the cigarette product 10 in order to inhale. In this operating status, the control arrangement 29 actuates the supply device 20, in order to supply fluid 50 from the fluid tank 18 as an addition 40 in the form of small drops of fluid as a mist/aerosol and/or in a gaseous form as vapor to the air flow 34.

Additionally or alternatively to the flow switch, the cigarette product can, for example, be switched on or off by means of a mechanical switch, a capacitive switch which is sensitive to the consumer touching the housing 11 or the mouth end 32, or touching a touchscreen.

The fluid to be dosed (i.e. the liquid component mixture), which is stored in the fluid tank 18, is, for example, a mixture of 1,2-propylene glycol, glycerin and/or water, to which one or more aromas (flavors) and/or active ingredients such as, for example, nicotine can be added.

The section containing the fluid tank 18 or the consumer unit 17 is advantageously executed as a cartridge 21 which can be replaced by the consumer, i.e. it is executed as a disposable part. The remainder of the cigarette product 10, in particular the section 13 containing the energy source 14, is advantageously executed as a basic part 56 which can be reused by the consumer, i.e. it is executed as a multi-way part. The cartridge 21 can be connected by the consumer to the basic part 56 and is configured such that it is detachable from the basic part 56. Consequently, a separation plane or respectively interface 57 is formed between the cartridge 21 and the reusable basic part 56.

The cartridge housing 58 can form a part of the housing 11 of the cigarette product 10.

Figure 2:
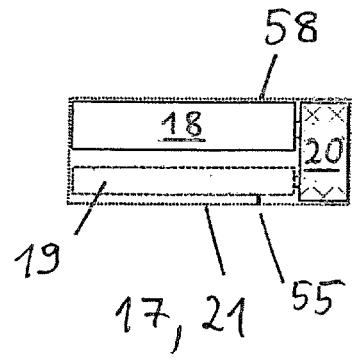
FIG. 2 shows a cross-sectional view of a cartridge for an electronic cigarette product.

In other embodiments, see FIG. 2, the consumer unit 17 is executed as a cartridge 21 which can be inserted by the consumer into the reusable basic part 56 of the cigarette product 10 and which can be extracted by the consumer therefrom.

The cartridge housing 58 is, in this case, a housing which is separate from the housing 11 of the cigarette product 10.

The cartridge 21 comprises at least the fluid tank 18. The cartridge 21 can, as shown in FIG. 2, comprise the electrical/electronic unit 19. In other embodiments, the electrical/electronic unit 19 can wholly or partly be a fixed part of the basic part 56. Likewise, the supply device 20 can be part of the cartridge 21 or can be arranged in the basic part 56. The cartridge 21 can therefore, in some embodiments, substantially only consist of the fluid tank 18 and, if necessary, the cartridge housing 58, wherein the cartridge housing 58 can alternatively be formed by the housing of the fluid tank 18, such that a separate cartridge housing 58 can be superfluous. A filling level monitoring device and/or display is/are preferably provided, which allow(s) the consumer to establish the filling level of the fluid tank 18.

In addition to being used in rod-shaped cigarette products 10, the cartridge 21 can also be used in other products, for example in an electronic pipe. As a general rule, the energy source 14 is not part of the cartridge 21, but part of the reusable basic part 56.

In one advantageous embodiment, the fluid tank 18 is a flexible bag. As a result, the fact that the fluid tank 18 can be emptied completely, independently of the location and in a leakage-free manner, is achieved with simple means. A typical tank volume of the fluid tank 18 lies in the range between 0.5 ml and 2 ml. The cigarette product 10 can advantageously comprise a level control for the fluid tank 18, which can be coupled, for example, to the number of puffs. The fluid tank 18 is preferably produced from an inert and/or food-grade material or respectively material suitable for pharmaceutical use, in particular a plastic, wherein the material can be visually transparent or opaque.

The fluid tank 18 can be mechanically coupled to the supply device 20 or decoupled from this. In the case of a mechanical coupling, the supply device 20 advantageously serves as a lid or leak protection for the fluid tank 18. In the case of a decoupling, a fluid line or respectively a capillary connection is, in particular, provided between the fluid tank 18 and the supply device 20. If the fluid tank 18 is executed in such a way that it can be separated from the supply device 20, this must be possible in a leakage-free manner, i.e. the fluid tank 18 has a locking mechanism which, as a consequence of the separation of the fluid tank 18 from the supply device 20, automatically seals a discharge opening of the fluid tank 18 in a fluid-tight manner, for instance by means of a spring-loaded ball, a non-return valve or the like. Different embodiments relating to the transport of fluid from the fluid tank 18 to the supply device 20 will be explained later with reference to FIGS. 6A to 6C.

The ratio of the largest extension a of the microsystems engineering unit 45 (see FIG. 3) to the average diameter D of the substantially rod-shaped housing 11 in the region of the supply device 20 (see FIG. 1) is advantageously less than 0.5.

Figure 3:
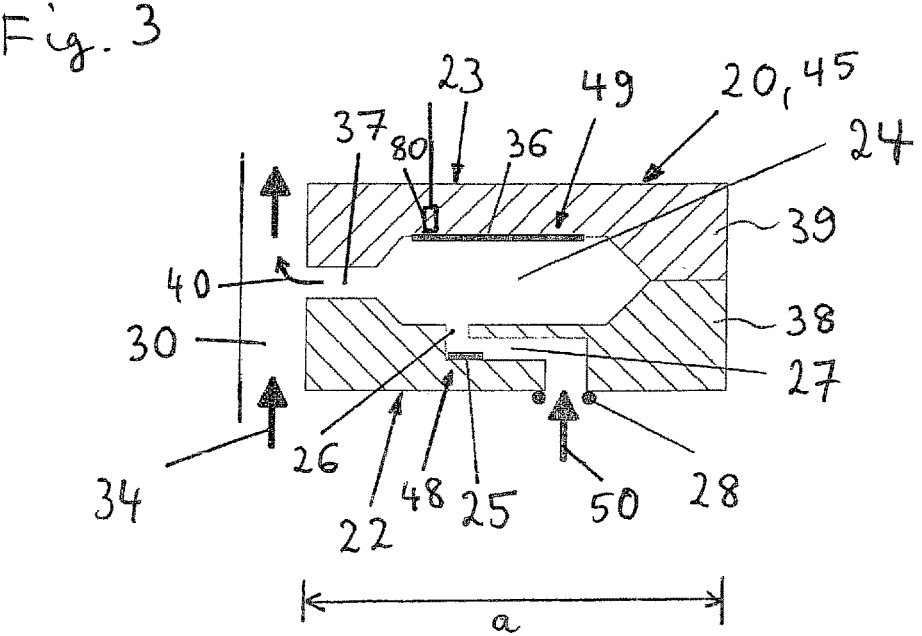
FIG. 3 shows a cross-sectional view of a supply device for an electronic cigarette product in an exemplary embodiment.

An advantageous embodiment of a supply device 20 according to the invention is shown in FIG. 3. The supply device 20 comprises an atomizer component part 22 having an atomizer 48 and an evaporator component part 23 having an evaporator 49, which are arranged with respect to a chamber 24 in the interior of the supply device 20.

The atomizer 48 is preferably a free-jet atomizer operating in accordance with the inkjet or bubblejet principle, having an actuator 25 arranged in a fluid channel 27 and a jet 26 arranged afterwards, which opens into the chamber 24. The actuator 25, which is electrically actuated with a suitable actuating frequency typically in the kHz range and, for example, between 10 Hz and 50 kHz, preferably between 100 Hz and 30 kHz, particularly preferably between 1 kHz and 25 kHz, can be a piezoelectric element or a heating element. On establishing an air flow 34 through the air channel 30, which is caused by the consumer drawing on the device, the control arrangement 29 actuates the actuator 25, wherein the fluid located in the fluid channel 27 is projected out of the jet 26 into the chamber 24 in the form of tiny droplets by means of sudden heating (in the case of a heating element) or by means of vibration (in the case of a piezoelectric element). The atomizer 48 simultaneously serves to deliver the fluid 50 from the fluid tank 18 through the fluid channel 27 and to dose the fluid in the chamber 24. The atomizer 48 can therefore also be referred to as a free-jet doser.

The atomizer/doser 48 is adjusted such that an advantageous fluid quantity in the range between 1 µl and 10 µl, typically 4 µl per puff of the consumer is introduced. The atomizer/doser 48 can preferably be adjusted in terms of the fluid quantity per puff.

The evaporator 49 has a heating device 36 which, on establishing an air flow 34 through the air channel 30, which is caused by the consumer drawing on the device, is actuated by the control arrangement 29, in order to be heated by means of current from the energy source and to evaporate the droplets exiting from the jet 26, i.e. to turn them into the gaseous or respectively vaporous state. In order to attain optimum evaporation, the heating device 36 is preferably arranged opposite the jet 26. The electrical heating device 36 can, in particular, comprise one or more plate-shaped heating elements.

The heating device 36 is controlled or regulated by the control arrangement 29, in particular the electrical/electronic unit 19, with respect to the evaporation temperature; this will be explained in even greater detail below. This can advantageously take place by controlling or regulating the heating capacity or the supplied heating energy. The temperature can be advantageously regulated on the basis of the measuring signal of a temperature sensor 80, for example a platinum measuring resistance or a resistance-variable conducting coating of the heating element 36.

Alternatively, the temperature of the heating device 36 can be indirectly determined and used to regulate the temperature, for example by means of the temperature dependence of the resistance of the heating device 36. The evaporative capacity preferably lies in the range between 1 W and 20 W, more preferably in the range between 2 W and 10 W. The evaporation temperature preferably lies in the range between 100° C. and 400° C. The effective area of the heating device 36 is preferably between 0.01 $mm^2$ and 9 $mm^2$, preferably between 0.05 $mm^2$ and 7 $mm^2$, particularly preferably between 0.1 $mm^2$ and 5 $mm^2$.

The liquid is evaporated at the heating device 36 without a time delay or with as low as possible a time delay at an exactly adjustable and regulated heating temperature, without the risk of local overheating.

This can be advantageously achieved by an electronically controlled or regulated temperature limiting of the heating device 36, for example, to the boiling temperature of a component which boils higher than the active ingredient, here 290° C.

The liquid quantity can advantageously be exactly adjusted and can be dosed independently of the evaporator capacity. Monitoring devices advantageously guarantee that only the planned liquid quantity is evaporated. Possible regulating strategies comprise the specification of a liquid delivery volume, or volume flow profile with corresponding tracking, via a puff. In this case, the dosed liquid quantity for each puff is advantageously always completely evaporated, in order to avoid a concentration at the heating device 36. The predefined upper temperature limit is not exceeded at any time in the liquid and/or in the gas phase in order to avoid pollutants being produced due to decomposition effects of the liquid constituents. Different quantities of vapor can advantageously be adjusted and evaporated by means of the liquid delivery, without contravening the requirements of the evaporation process indicated above. Monitoring devices advantageously guarantee that only the exactly adjusted quantity of liquid to be dosed is evaporated in each case. For this purpose, sensor technology is advantageously provided in order to monitor the correct function of the cigarette product 10.

The combination of atomizer/evaporator can be advantageously adjusted such that fluid particles having a diameter in the range between 0.5 μm and 5 μm, preferably between 1 μm and 3 μm, are mainly produced. Particle sizes in the range between 0.5 and 2 MMAD (mass median aerodynamic diameter), preferably between 0.7 and 1.5 MMAD, for example around approx. 1 MMAD can be optimal. MMAD corresponds to an EU standard and is specified in μm.

Diameters of less than 1 μm, for example in the range between 0.7 μm and 1 μm, cannot typically be achieved by pure atomization, requiring instead the evaporation of the fluid followed by retrograde condensation from the gas phase. However, (pre)atomization can, in certain circumstances, facilitate the evaporation. In one embodiment, a release of active ingredients which is as uniform as possible is to be guaranteed for each puff.

In order to make different smoker profiles possible, a reserve in the evaporator capacity is advantageously provided.

Since the chamber 24 is in particular used to evaporate the droplets exiting from the jet 26, the chamber 24 can also be referred to as an evaporator chamber. The chamber 24 is advantageously oblong in cross-section, as shown for example in FIG. 3, wherein the jet 26 and the heating element 36 are advantageously arranged on opposite longitudinal sides. An outlet bore 37 is preferably provided perpendicularly or laterally to the exit direction of the fluid jet from the jet 26, through which outlet bore the vapor generated by the evaporator 49 exits from the evaporator chamber 24, where it is carried along and absorbed by the air flow 34 which preferably extends perpendicularly to the bore 37.

Since the actuator 25 of the atomizer 22 and the heating element 36 of the evaporator 23 are electrically connected separately to the control arrangement 29 and actuated separately from one another, an advantageous functional separation between the delivery/dosing/atomization, on the one hand, and the evaporation, on the other hand, is achieved.

The fluid channel 27 is preferably sealed by means of a gasket 28 arranged between the supply device 20 and the fluid tank 18 and surrounding the orifice of the fluid channel 27 externally.

The vapor or respectively the aerosol 40 is supplied to the air flow 34, in that this flows past the outlet opening 42 of the evaporator chamber 24 externally, see FIGS. 1 and 3. In alternative embodiments, the air flow 34 flows through the supply device 20 and the vapor or respectively the aerosol 40 is carried along or absorbed by the air flow 34 in the evaporator chamber 24. The supply device 20 can be arranged at a distance from the mouth end 32 of the cigarette product 10, in particular in the region of the interface 57 between the cartridge 21 and the basic part 56, as in the embodiment example according to FIG. 1. The supply device 20 can alternatively be arranged close to the mouth end 32 of the cigarette product 10. An arrangement lateral to the fluid tank 18, in particular in the region of the electrical/electronic unit 19, is also possible.

In the embodiment according to FIG. 3, both the atomizer component part 22 and the evaporator component part 23 are executed using microsystems engineering on a substrate 38, for example made of a polymer, glass, ceramic, metal, metalloid, e.g. silicon, silicon compounds or metal oxide compounds. Microsystems engineering units have electrical and/or mechanical structures with dimensions in the micrometer or respectively sub-millimeter range, which are incorporated into a substrate using a standard processing operation. In the case of an atomizer component part 22, the fluid channel 27, the electrical actuator 25 and, if necessary, sensor technology provided in the atomizer component part 22 are, in particular, incorporated into the substrate 38 in a standard microsystems engineering processing operation. In the case of an evaporator component part 23, the heating element 36 and, if necessary, a piezoelectric element for vibrating the heating element 36 and sensor technology provided in the evaporator component part 23 are, in particular, incorporated into the substrate 38 using a standard microsystems engineering processing operation. In the embodiment according to FIG. 3, the entire supply device 20 is therefore executed as a standard microsystems engineering unit 45.

In the embodiment according to FIG. 3, the heating element 36 is flat and parallel to the surface of the substrate 39, that is to say it is arranged virtually "lying". Other embodiments are possible. Preheating with an electrical preheating element and a preheating chamber can be arranged in the fluid channel 27.

In one embodiment, which is not shown, only the atomizer component part 22 is configured as a microsystems engineering unit 45, while the substrate 39 of the evaporator component part 23 is produced from a non-conducting material, in particular glass, ceramic or a plastic. This construction can be less expensive and consequently advantageous.

The consumer unit 17 or respectively the cartridge 21 advantageously comprises a non-volatile information store 53 (see FIG. 1) for storing information or respectively parameters relating to the consumer unit 17 or respectively the cartridge 21, for example executed as an EEPROM, RFID or other suitable form. The information store 53 can be configured as part of the electrical/electronic unit 19 or separately therefrom. Information regarding the constituent, i.e. regarding the composition of the fluid stored in the fluid tank 18 is advantageously stored in the information store 53; information regarding the process profile, in particular capacity/temperature control; data regarding status monitoring or respectively system testing, for example leak testing; data relating to copy protection and forgery-proofness, in particular comprising an ID in order to clearly identify the consumer unit 17 or respectively cartridge 21; serial number, manufacturing date and/or expiry date; and/or number of puffs (number of inhalation puffs by the consumer) or respectively the usage time. The data store 53 is or can advantageously be connected via contacts and/or lines to the control device 15 of the basic part 56.

An electrical connection 54 is advantageously provided between the consumer unit 17 or respectively the cartridge 21 and the energy supply unit 12 via a corresponding electrical interface 55 which makes it possible to replace the cartridge 21. The electrical connection 54 serves, on the one hand, to exchange data between the consumer unit 17 or respectively the cartridge 21 and the energy supply unit 12 and, on the other hand, to supply power to the consumer unit 17 or respectively the cartridge 21 through the electrical energy source 14.

The energy supply unit 12 or respectively the basic part 56 can advantageously have a charging interface 60 for charging up the energy source 14. The charging interface 60 can, for example, make possible charging up by induction or direct electrical coupling. Instead of a charging interface, the energy source can also be configured as a replacement storage battery or replacement battery, wherein a discharged energy source 14 can be extracted by the consumer from the cigarette product 10 and a charged energy source 14 can be reinserted. Embodiments having a disposable energy source 14, in particular a battery, without a charging interface 60 are also conceivable, wherein the basic part is disposed of following discharging of the energy source 14.

In all of the embodiments shown in the figures, the consumer unit 17 or respectively the cartridge 21 has an electrical control unit 19 and further electrical components, in particular actuators 25 and heating elements 36. However, embodiments are also possible, in which the electrical control unit 19 and/or the further electrical components are completely arranged in the reusable basic part 56, such that the number of electrical components in the consumer unit 17 or respectively cartridge 21 is reduced, or the consumer unit 17 or respectively cartridge 21 comprises at most passive electrical components (passive data store 53 such as RFID, transponder or the like), or is free of electrical components. The advantage of these embodiments is that an electrical contacting of the cartridge 21 via the electrical interface 55 can be advantageously dispensed with.

The universal relationship between the liquid composition, the temperature behavior during evaporation and the active ingredient release, which was discovered according to the invention, is explained below with reference to the diagrams in FIGS. 4A to 4D. These curves were calculated, by way of example, for a reference component mixture having 63 percent by weight of propylene glycol (PG), 29.85 percent by weight of pure glycerin (Gl.), 5.15 percent by weight of water ($H_2O$) and 2 percent by weight of nicotine (N), assuming open evaporation, i.e. the vapor (gas phase) is continually removed. Furthermore, FIGS. 4A to 4D relate to the case where an initial fluid mass is completely evaporated. (This is to be distinguished from the case which is referred to as a "refill" where the fluid mass is kept constant by subsequent delivery of further fluid).

All of the curves are plotted using the relationship $m_G/m_{L,0}$ of the evaporated mass $m_G$ based on the initial mass $m_{L_o}$ of the entire liquid. FIG. 4A shows the remaining mass $m_{L,i}$ (i=component index) in the liquid phase for propylene glycol (PG), glycerin (Gl.), water (H$_2$O), nicotine (N) as well as for the total of all components (to.=total) based on the initial mass $m_u$ of the entire liquid. FIG. 4B shows the mass fractions $w_{G,i}$ in the gas phase in percent for propylene glycol (PG), glycerin (Gl.), water (H$_2$O) and nicotine (N). FIG. 4C shows the same mass fractions $w_{L,i}$ in the liquid phase in percent. FIG. 4D shows the boiling temperature $T_B$ in ° C. of the component mixture, assuming isobar evaporation.

FIG. 4B is particularly instructive, since it shows the change in the composition of the vapor (gas phase) inhaled by the consumer. It is clear from FIG. 4B that the components water, propylene glycol and glycerin are substantially not evaporated azeotropically, but mainly successively, wherein the sequence is determined by the respective boiling temperatures. The evaporation of nicotine can be bound to the evaporation of propylene glycol and/or can be maximal between the evaporation of propylene glycol and that of glycerin. In any case, the nicotine is substantially already completely evaporated in the last section of time when glycerin is substantially evaporated, see also FIG. 4C. It is obvious that the concentration and effectiveness of the active ingredient nicotine, as well as the length of time of the addition of the active ingredient, can be controlled by the proportion of glycerin (in general of the higher boiling component or of a higher boiling component) in the component mixture.

If the evaporator temperature (temperature of the heating device 36) is advantageously selected, for instance in the range between the boiling temperature of the active ingredient and the boiling temperature of the higher boiling component or of a higher boiling component, here for example in the range between 250° C. and 290° C., preferably in the range between 260° C. and 290° C., more preferably in the range between 270° C. and 290° C., for example at approximately 280° C., the temperature curve of the heating device 36 follows the curve shown in FIG. 4D until it reaches the adjusted maximum temperature (for example 280° C.), which is however no longer sufficient to effectively evaporate the higher boiling component (here: glycerin). The consumer will realize from the lack of vapor being developed that the proportion of the active ingredient in the contents of the cartridge has been used up, and will replace the used-up cartridge 21, which may still contain a considerable proportion of the higher boiling (dummy) component (glycerin), with a new cartridge 21.

The universal curves shown in FIGS. 4A to 4D can be calculated for each relevant component mixture or can be measured for each calibration. The optimum evaporating parameters can be deduced for each relevant component mixture from the universal evaporation curves and are stored by the manufacturer in a data store 59 of the basic part 56. The data store 59 is advantageously provided in the electronic unit 15 of the basic part 56. When a new cartridge 21 is inserted into the cigarette product 10, the electronic control device 15 of the basic part 56 reads out the identification of the cartridge 21, which is stored in the data store 53 of the cartridge 21 and which clearly describes the component mixture contained in the cartridge 21, from the data store 53, loads the set of evaporating parameters which are clearly assigned to the identification from the data store 59 of the basic part 56, and controls the atomizer 48 and/or the evaporator 49 on the basis of the read-in set of evaporating parameters. In this way, optimum evaporation is automatically guaranteed for each component mixture. It is also possible to store the evaporation parameters in the data store 53 of the cartridge 21 so that they can be read out by the electronic control device 15. In this case, storage in the data store 59 of the basic part 56 can be superfluous.

Figure 5:
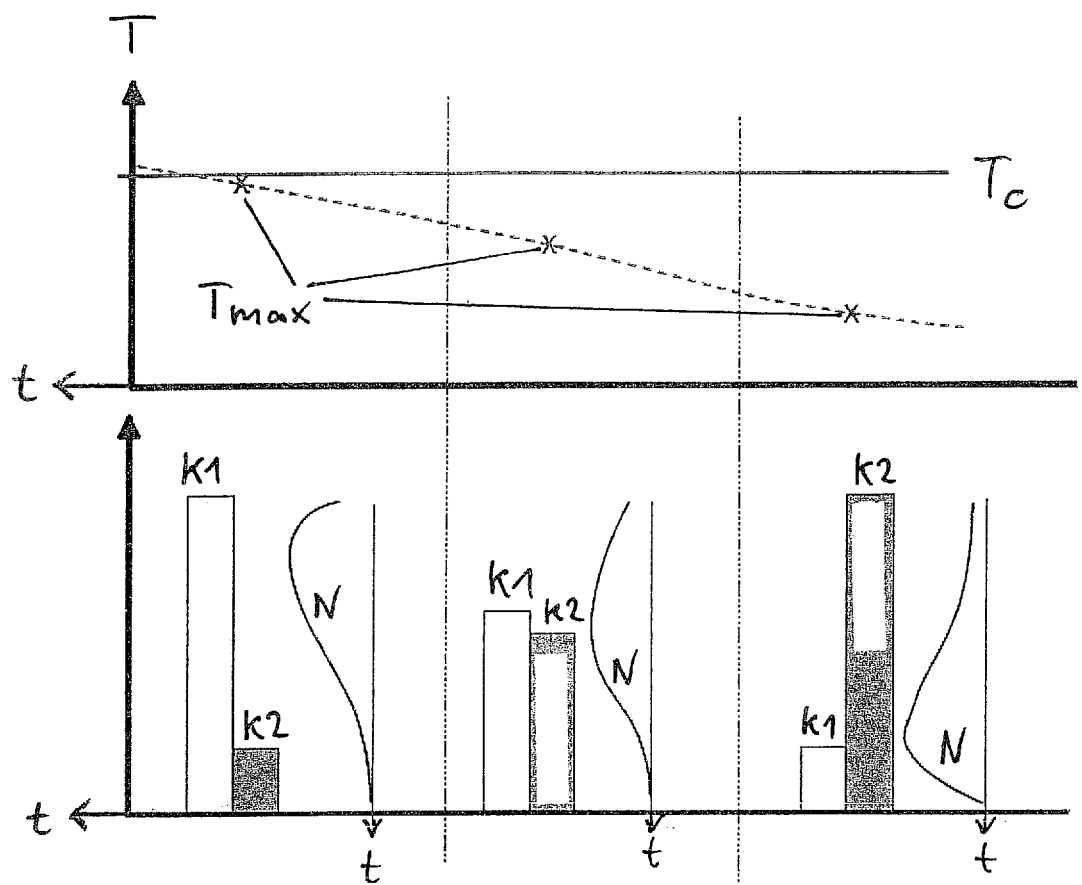
FIG. 5 shows diagrams regarding the evaporation behavior of a component mixture having different component proportions and/or at different points of the cartridge emptying.

The diagram in FIG. 5 illustrates, on the one hand, the targeted use of the liquid composition for influencing the active ingredient release at a given or respectively adjusted threshold temperature (maximum temperature) of the evaporator. The lower part of FIG. 5 shows three different component mixtures. In the left case, the component K1 outweighs the component K2. In the middle case, the components K1 and K2 have approximately comparable proportions. In the right case, the component K2 outweighs the component K1. The component K1 could, for example, boil higher, the component K2 could boil lower, than the active ingredient. It is clear from the upper part of FIG. 5 that the maximum temperature of the evaporator $T_{max}$ changes according to the respective proportions of the component mixture. In each case, the maximum temperature of the evaporator $T_{max}$ should be below the critical temperature $T_c$, which marks the threshold for the release of pollutants.

The courses of the curves in the lower part of FIG. 5 show the temporal progress of the active ingredient release. In the left case, the active ingredient (for instance nicotine N) is mainly released relatively early on, in the middle case the maximum quantity of the active ingredient is released in the central region of time, whilst, in the right case, the active ingredient is mainly released relatively late on. This illustrates how the temporal progress of the active ingredient release can be deliberately adjusted or respectively controlled by selecting the proportions of the component of the component mixture.

On the other hand, FIG. 5 can also represent a change in the component proportions over time during the emptying of the cartridge as a consequence of partial segregation of the component mixture. In this case, the horizontal axis in FIG. 5 is a time axis which here runs from right to left, corresponding to a maximum temperature $T_{max}$ which rises over time.

As explained below, FIG. 5 depicts, in connection with FIGS. 6A to 6C, three substantially different operating methods or respectively technologies of the inhaler.

Figure 6A:
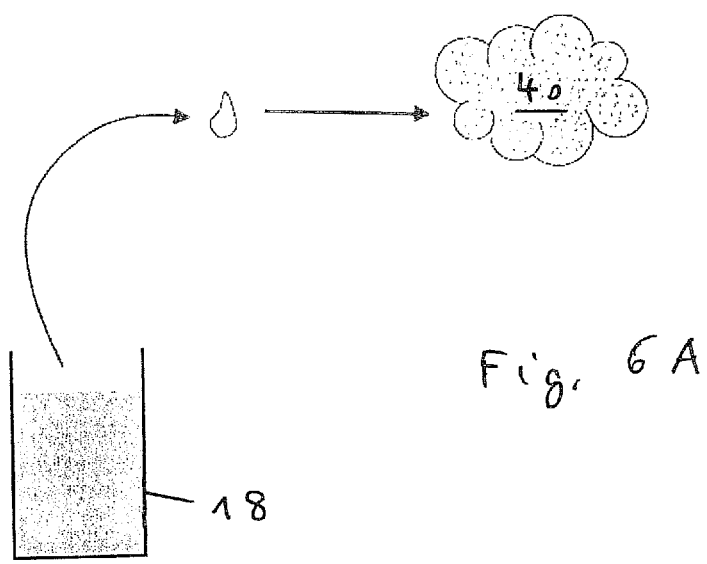
FIGS. 6A-6C show schematic representations of different embodiments relating to the transport of fluid from the tank to the supply device.
Figure 6B:
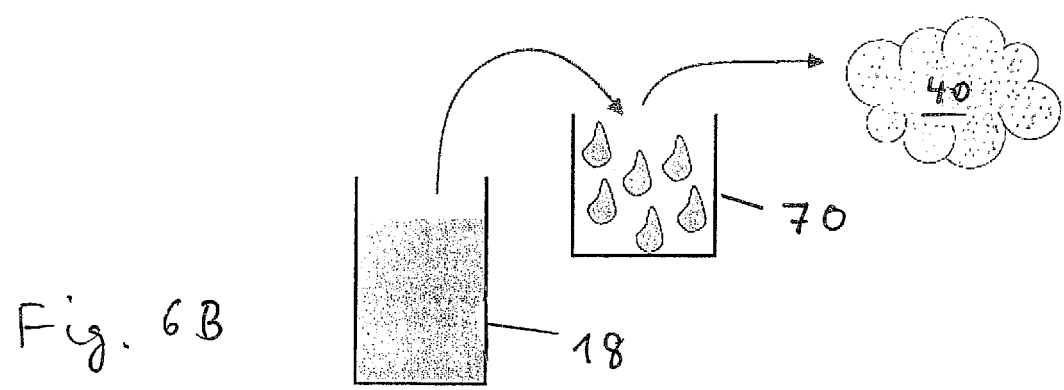
Figure 6C:
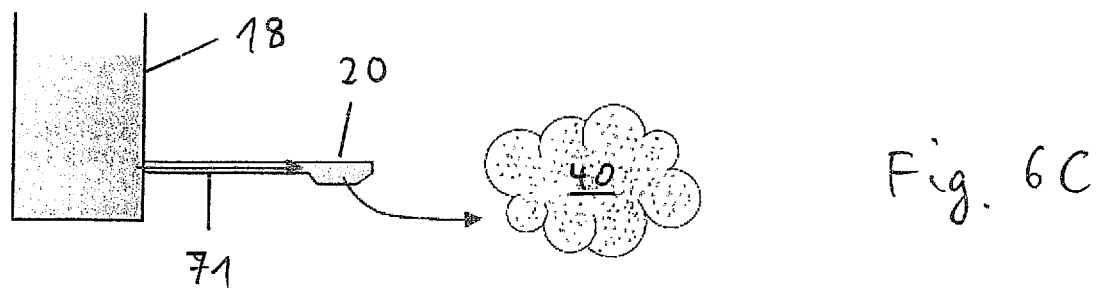

FIGS. 6A to 6C illustrate how the evaporation behavior and the active ingredient release can be deliberately influenced by transporting the fluid from the fluid tank 18 to the supply device 20 or respectively to the evaporator 49 in different ways.

FIG. 6A relates to an active delivery of the fluid, which is accurate to the last droplet, from the fluid tank 18 to the evaporator 49 in order to generate the vapor 40. A typical embodiment example of this would be a free-jet atomizer 48 operating in accordance with the inkjet or bubblejet principle. This variant results in a defined, uniform active ingredient release or respectively dosing per puff, in particular independently of the respective fluid composition. The liquid quantity which is supplied once only or in a pulsed manner is evaporated completely. Due to the fact that the heating device 36 is advantageously controlled or regulated at the maximum required temperature $T_{max}$ for evaporating the highest-boiling individual component of the liquid, this variant remains free of liquid residue following the evaporation process. The composition of the vapor corresponds, with each puff, to the initial composition of the liquid.

Corresponding to this, the active ingredient release is therefore shown in FIG. 5 as a function of the volume proportion of a higher boiling component for three different, independent liquids. Whenever the fluid composition is kept constant for each inhalation/smoker puff, the active ingredient release will also remain the same for each puff. When this technology is implemented, this corresponds to FIG. 6A, in which a drop having an identical composition is supplied to the evaporation.

Consequently, no segregation takes place in the actual reservoir.

FIG. 6B relates to an active delivery to the evaporator 49 by means of an intermediate reservoir 70 which is either arranged in the cartridge 21 or in the basic part 56.

This variant results in a controlled active ingredient release by means of a defined number of puffs during evaporation from the intermediate reservoir 70. A segregation of the fluid takes place in the intermediate reservoir 70 depending on the fluid composition and the permitted maximum temperature $T_{max}$ of the evaporator. In this variant, the evaporator is advantageously controlled or regulated at a temperature below or equal to the required temperature $T_{max}$ for evaporating the highest-boiling individual component of the liquid. The liquid composition determines the concentration and temporal release of the active ingredient in the vapor. The liquid quantity which is supplied once only or in a pulsed manner to the intermediate reservoir 70 is completely evaporated during the defined number of puffs.

FIG. 6C relates to a passive delivery by means of a transport device 71, for example a pipe, to the supply device 20 or respectively the evaporator 49. This variant results in a controlled active ingredient release, in particular by regulating the evaporation temperature at a value below the required temperature $T_{max}$ for evaporating the highest-boiling individual component of the liquid. A segregation of the fluid takes place in the fluid tank 18 depending on the fluid composition and the permitted maximum temperature $T_{max}$ of the evaporator. As a result, the active ingredient is deliberately expelled, without the entire contents of the liquid reservoir being evaporated. The active ingredient concentration in the vapor is increased with respect to the active ingredient concentration in the liquid. Before the highest-boiling individual component is converted to the gas phase, no more active ingredient is left in the fluid tank 18. By limiting the evaporation temperature, the system switches off before pollutants can be emitted.

Therefore, as soon as segregation can take place in a(n) (intermediate) reservoir 70, 18, FIG. 6B or respectively 6C, FIG. 5 depicts the slow temporal segregation of the liquid (from right to left in FIG. 5) at three exemplary points, that is to say on the overriding horizontal time scale, the change in time of the active ingredient release per puff and, parallel thereto, the increase in the system temperature required for the evaporation, since the temperature progresses proportionally to the increase in the proportion of the highest-boiling component, similarly to FIGS. 4C and 4D.

The realization described in FIGS. 4A to 4D therefore makes it possible, with the available hardware, FIGS. 6A to 6C, to realize three different regulating concepts for the respective corresponding hardware.

EMBODIMENTS

Embodiment 1. An inhaler comprising a housing (11) with a mouth end (32), at least one air inlet opening (31) and an air channel (30) extending in the housing between the at least one air inlet opening (31) and the mouth end (32), a receiving area for a fluid reservoir (18), an electrical energy source (14), a supply device (20) for generating vapor and/or aerosol from a component mixture (50) extracted from the fluid reservoir (18) and adding the vapor and/or the aerosol (40) to an air flow (34) flowing in the air channel (30), wherein the supply device (20) has an evaporator (49) which can be actuated separately, and a control device (29) for controlling the supply device (20), characterized in that the control device (29) is connected or can be connected to a data store (53; 59) in which at least one set of predefined evaporating parameters is stored and can be called upon for evaporating the component mixture in the evaporator (49).

Embodiment 2. The inhaler according to Embodiment 1, characterized in that the at least one set of predefined evaporating parameters contains data regarding one or more variables from the following group of variables:
a temperature to be adjusted;
a duration of individual evaporation steps and/or of the entire evaporation process, which is to be adjusted;
a pressure to be adjusted;
an evaporation energy to be provided.

Embodiment 3. The inhaler according to any one of the preceding Embodiments, characterized in that the at least one set of predefined evaporating parameters contains data regarding one or more variables from the following group of variables:
a minimum temperature and/or a maximum temperature;
a minimum pressure and/or a maximum pressure;
a minimum duration and/or a maximum duration of individual evaporation steps and/or of the entire evaporation process.

Embodiment 4. The inhaler according to any one of the preceding Embodiments, characterized in that the at least one set of predefined evaporating parameters is deduced from the liquid phase-gas phase equilibrium diagram of the component mixture or corresponds thereto.

Embodiment 5. The inhaler according to the preamble of Embodiment 1 or according to any one of the preceding Embodiments, characterized in that the control device (29) is set up to keep the temperature of the evaporator (49), at least over an evaporation interval corresponding to an inhalation puff, above a first characteristic temperature, in particular the boiling temperature of a component of the component mixture.

Embodiment 6. The inhaler according to Embodiment 5, characterized in that the predefined temperature value lies in the range between 1% and 90%, preferably 3% to 70%, particularly preferably 5% to 50% above the first characteristic temperature.

Embodiment 7. The inhaler according to the preamble of Embodiment 1 or according to any one of the preceding Embodiments, characterized in that the control device (29) is set up to keep the temperature of the evaporator (49), at least over an evaporation interval, below a second characteristic temperature, in particular the boiling temperature of a component of the component mixture.

Embodiment 8. The inhaler according to Embodiment 7, characterized in that the second characteristic temperature is the boiling temperature of a highest-boiling component of the component mixture.

Embodiment 9. The inhaler according to any one of Embodiments 5 to 8, characterized in that
the evaporation interval has a duration of 1 to 12 seconds, preferably 2 to 8 seconds.

Embodiment 10. The inhaler according to any one of the preceding Embodiments, characterized in that the evaporator (49) comprises a heating device (36) which can be adjusted to a predefined temperature.

Embodiment 11. The inhaler according to Embodiment 10, characterized in that the evaporator (49) has a temperature sensor (80) for measuring the temperature of the heating device (36) and/or for controlling or regulating the temperature of the heating device (36).

Embodiment 12. The inhaler according to Embodiment 10 or 11, characterized in that the predefined temperature is variable within an evaporation interval, in particular it intermittently increases and/or intermittently falls and/or is intermittently constant over the duration of an evaporation interval.

Embodiment 13. The inhaler according to any one of the preceding Embodiments, characterized in that a maximum temperature of the evaporator is at most 350° C., preferably at most 300° C. and, particularly preferably, at most 290° C.

Embodiment 14. The inhaler according to any one of the preceding Embodiments, characterized in that a machine-readable identification of the component mixture is assigned to the fluid reservoir (18), which is or can preferably be stored in the data store (53).

Embodiment 15. The inhaler according to any one of the preceding Embodiments, characterized in that the evaporation behavior is influenced in a deliberate manner, and the active ingredient released, by means of a suitably designed transport of the fluid from the fluid tank (18) to the supply device (20)

Embodiment 16. The inhaler according to Embodiment 15, characterized in that the fluid is transported from the fluid tank (18) to the supply device (20) by means of an intermediate reservoir (70).

Embodiment 17. The inhaler according to Embodiment 15 or 16, characterized in that the evaporator (49) is connected or can be connected to the fluid reservoir (18) permanently by means of a line (71), or interruptibly in a fluid-conducting manner in order to form predefined fluid portions.

Embodiment 18. The inhaler according to any one of Embodiments 15 to 17, characterized in that the supply device (20) has a drop atomizer (48) which conducts the fluid drop by drop to the heating device (36) which is arranged at a distance.

Embodiment 19. A fluid reservoir for an inhaler according to any one of the preceding Embodiment, containing a component mixture, characterized in that the proportion of a component of the component mixture, for example glycerin, which boils higher than an active ingredient component, for example nicotine, lies in the range between 15 percent by weight and 98 percent by weight and/or is at least 44 percent by weight.

The invention claimed is:

1. An inhaler, comprising:
a housing,
wherein the housing comprises;
 a mouth end;
 at least one air inlet opening; and
 an air channel extending in the housing between the at least one air inlet opening and the mouth end;
a fluid reservoir for storing component mixture;
a receiving area for the fluid reservoir;
an electrical energy source that provides heating energy;
a supply device for generating vapor and/or aerosol from a component mixture extracted from the fluid reservoir and adding the vapor and/or the aerosol to an air flow flowing in the air channel,
wherein the supply device comprises a controllable evaporator that can be actuated separately; and
a control device that controls the supply device and is connected to a data store comprising at least one set of predefined evaporating parameters, deduced from a liquid phase-gas phase equilibrium diagram for the component mixture, which are called upon for evaporating a component mixture in the evaporator,
such that, when heating energy is retrieved for evaporation of the component mixture, the control device calls upon the evaporating parameters in the data store to control the heating energy thereby adjusting an instantaneous vapor composition by controlling the evaporation of the component mixture.

2. The inhaler according to claim 1, further comprising an electrical heating device operably connected to the electrical energy source,
wherein the at least one set of predefined evaporating parameters contains data regarding one or more variables from the following group of variables:
 a temperature of the heating device to be adjusted;
 at least one of a duration of individual evaporation steps and the entire evaporation process, which is to be adjusted;
 a pressure to be adjusted in an atomizer; and
 an evaporation energy to be provided for the evaporator.

3. The inhaler according to claim 1, further comprising an electrical heating device,
wherein the at least one set of predefined evaporating parameters contains data regarding one or more variables from the following group of variables:
 a minimum temperature of the heating device;
 a maximum temperature of the heating device;
 a minimum pressure in the atomizer;
 a maximum pressure in the atomizer;
 a minimum duration of at least one of the individual evaporation steps and the entire evaporation process; and
 a maximum duration of at least one of the individual evaporation steps and the entire evaporation process.

4. The inhaler according to claim 1,
wherein the at least one set of predefined evaporating parameters corresponds to the liquid phase-gas phase equilibrium diagram of the component mixture.

5. The inhaler according to claim 1,
wherein the control device keeps the temperature of the evaporator, at least over an evaporation interval corresponding to an inhalation puff, above a first characteristic temperature, comprising the boiling temperature of a component of the component mixture.

6. The inhaler according to claim 5,
wherein the control device keeps the temperature of the evaporator in a range of between 1% and 90%, between 3% and 70%, or between 5% and 50%, above the first characteristic temperature.

7. The inhaler according to claim 1,
wherein the control device keeps a temperature of the evaporator, at least over an evaporation interval, below a second characteristic temperature comprising the boiling temperature of a component of the component mixture.

8. The inhaler according to claim 7,
wherein the second characteristic temperature is the boiling temperature of a highest-boiling component of the component mixture.
9. The inhaler according to claim 8,
wherein the evaporation interval has a duration of between 1 to 12 seconds or between 2 to 8 seconds.
10. The inhaler according to claim 1,
wherein the evaporator comprises a heating device that is adjustable to a predefined temperature.
11. The inhaler according to claim 10,
wherein the evaporator comprises temperature sensor that peroforms at least one of measuring a temperature of the heating device and controlling or regulating a temperature of the heating device.
12. The inhaler according to claim 10,
wherein the predefined temperature is variable within an evaporation interval, including one or more of the following:
intermittently increasing;
intermittently falling; and
intermittently constant;
over the duration of an evaporation interval.
13. The inhaler according to claim 1,
wherein a maximum temperature of the evaporator is at most 350° C., at most 300° C., or at most 290° C.
14. The inhaler according to claim 1,
wherein a machine-readable identification of the component mixture is assigned to the fluid reservoir, which is stored in the data store.
15. The inhaler according to claim 1,
wherein evaporation is controlled, and an active ingredient is released, via transport of the component mixture from the fluid reservoir to the supply device.
16. The inhaler according to claim 15, further comprising an intermediate reservoir through which the component mixture is transported from the fluid reservoir to the supply device.
17. The inhaler according to claim 15,
wherein the evaporator is permanently fluidly-connected or interruptedly fluidly-connected to the fluid reservoir via a line to form predefined fluid portions.
18. The inhaler according to claim 15,
wherein the supply device has a drop atomizer which conducts the fluid drop by drop to the heating device which is arranged at a distance.
19. The inhaler, according to claim 1, further comprising fluid reservoir that contains a component mixture,
wherein a proportion of a component of the component mixture, which boils higher than an active ingredient component, lies in a range between 15 percent by weight and 98 percent by weight or is at least 44 percent by weight.
20. The inhaler, according to claim 1, wherein the heating energy retrieved at any time during the evaporation is used to conclude a current liquid or vapor composition, wherein the current liquid or vapor composition detected in this way is used to control the evaporation of the component mixture.

* * * * *